(12) United States Patent
Forquy et al.

(10) Patent No.: US 8,791,292 B2
(45) Date of Patent: Jul. 29, 2014

(54) DIMETHYL DISULPHIDE DERIVED AT LEAST PARTIALLY FROM RENEWABLE MATERIALS

(75) Inventors: Christian Forquy, Monein (FR); Georges Fremy, Sauveterre de Bearn (FR)

(73) Assignee: Arkema France, Colombes (FR)

( * ) Notice: Subject to any disclaimer, the term of this patent is extended or adjusted under 35 U.S.C. 154(b) by 51 days.

(21) Appl. No.: 13/058,394

(22) PCT Filed: Aug. 18, 2009

(86) PCT No.: PCT/FR2009/051592
§ 371 (c)(1),
(2), (4) Date: Mar. 8, 2011

(87) PCT Pub. No.: WO2010/020729
PCT Pub. Date: Feb. 25, 2010

(65) Prior Publication Data
US 2011/0172138 A1    Jul. 14, 2011

(30) Foreign Application Priority Data
Aug. 20, 2008   (FR) .................................... 08 55630

(51) Int. Cl.
*C07C 309/00* (2006.01)
*C07C 321/00* (2006.01)

(52) U.S. Cl.
USPC .......................................... 562/112; 568/21

(58) Field of Classification Search
USPC .......................................... 568/21; 562/112
See application file for complete search history.

(56) References Cited

U.S. PATENT DOCUMENTS

| 4,280,966 | A | * | 7/1981 | Hubenett | 562/829 |
| 5,698,830 | A | * | 12/1997 | Lacombe et al. | 204/157.15 |
| 6,124,497 | A | * | 9/2000 | Chen | 562/118 |
| 6,531,629 | B1 | * | 3/2003 | Eiermann et al. | 562/118 |
| 6,743,951 | B2 | * | 6/2004 | Fremy | 568/21 |
| 7,365,233 | B2 | * | 4/2008 | Stauffer | 568/70 |
| 7,470,825 | B2 | * | 12/2008 | Lattner | 568/909 |
| 7,700,816 | B2 | * | 4/2010 | Xu et al. | 585/640 |
| 7,854,774 | B2 | * | 12/2010 | Renninger et al. | 44/451 |

FOREIGN PATENT DOCUMENTS

| EP | 0202420 B1 | * | 1/1991 |
| JP | 11188262 A | * | 7/1999 |

OTHER PUBLICATIONS

Meinardi S. et al. (2003) "Dimethyl Disulfide (DMDS) and Dimethyl Sulfide (DMS) Emissions from Biomass Burning in Australia" Geophysical Research Letters, 30(9) 7-1-7-4.

* cited by examiner

*Primary Examiner* — Fereydoun G Sajjadi
*Assistant Examiner* — Kofi Adzamli
(74) *Attorney, Agent, or Firm* — Smith, Gambrell & Russell, LLP

(57) ABSTRACT

One subject of the invention is a dimethyl disulphide in which the content of biocarbon is at least 1%. Another subject of the invention is processes for preparing this dimethyl disulphide. Yet another subject of the invention is the use of such a dimethyl disulphide for the manufacture of methanesulphonic acid.

4 Claims, No Drawings

DIMETHYL DISULPHIDE DERIVED AT LEAST PARTIALLY FROM RENEWABLE MATERIALS

FIELD OF THE INVENTION

The invention relates to disulfides, in particular dimethyl disulfide (DMDS), and to a process for its preparation starting from renewable raw materials. The invention also relates to the use of said DMDS for the preparation of methanesulfonic acid.

BACKGROUND OF THE INVENTION

Dimethyl disulfide with formula H3C—S—S—CH3, hereinafter termed DMDS, but which can also be termed methyl dithiomethane, is used in a large number of applications. DMDS is used in particular as a sulfiding agent or pre-sulfiding agent in refineries for the activation of hydrotreatment catalysts. DMDS is also used in the petrochemical products industry to protect steam cracking circuits from coke and carbon monoxide formation. It may also be used as an intermediate in fine chemicals synthesis or in metallurgy for its anti-corrosion properties. Furthermore, it may be used as a pesticide and as a fumigation agent in agriculture.

Dimethyl disulfide (DMDS) is a product which is widely available; in particular, it is marketed by ARKEMA.

DMDS is synthesized from conventional hydrocarbon-containing compounds, namely those derived from the oil industry. Although DMDS is not dangerous to the ozone layer, the ecological balance of its production is not perfect, especially as regards the $CO_2$ balance, and current processes for the manufacture of DMDS contribute further to climatic warming.

Thus, the aim of the invention is to reduce global warming during the manufacture of dimethyl disulfide, by reducing the emissions of greenhouse gases linked to their manufacture.

Thus, the aim of the invention is to improve the carbon footprint (cumulative greenhouse gas emissions linked to the production of raw materials and to the production process) of polysulfides.

SUMMARY OF THE INVENTION

The invention provides a dimethyl disulfide with formula $CH_3$—S—S—$CH_3$ with a bio-carbon content of at least 1%.

In accordance with one embodiment, the bio-carbon content is more than 5%, preferably more than 10%, preferably more than 25%, preferably more than 50%, preferably more than 75%, preferably more than 90%, preferably more than 95%, preferably more than 98%, preferably more than 99%, advantageously substantially 100%.

The invention also provides a process for the preparation of dimethyl disulfide in accordance with the invention, comprising a step for providing one or more carbon chains containing one or more carbon-containing atoms with a bio-carbon content of at least 1%, and transformation into DMDS by synthesis.

According to one implementation, the provision step includes a step for producing methanol.

According to one implementation, the methanol production step is carried out by biomass fermentation.

According to one implementation, the methanol production step comprises the following sub-steps: (i) producing methane from biomass; (ii) steam reforming thereof to a synthesis gas or production of synthesis gas by direct biomass gasification; and (iii) producing methanol from said synthesis gas.

According to one implementation, the methanol production step comprises the following sub-steps: (i) producing methane from biomass; (ii) oxidizing methane directly to methanol.

According to one implementation, the synthesis comprises at least one step for the transformation of methanol into methylmercaptan by reacting methanol with hydrogen sulfide, and a step for the transformation of methylmercaptan into dimethyl disulfide by oxidizing methylmercaptan using sulfur.

According to an alternative production mode, the methylmercaptan may also be synthesized from synthesis gas derived from biomass by the direct reaction of synthesis gas with hydrogen sulfide using a catalytic process without passing via methanol. The overall reaction in this case is written as follows:

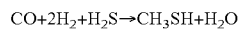

$$CO+2H_2+H_2S \rightarrow CH_3SH+H_2O$$

Advantageously, in this process, said provision step comprises at least one step for producing methylmercaptan.

Advantageously, the methylmercaptan production step comprises the following sub-steps: (i) producing methane from biomass; (ii) steam reforming it to form a synthesis gas; and (iii) producing methylmercaptan directly from said synthesis gas by reacting said synthesis gas with hydrogen sulfide.

Advantageously, in this process, said synthesis step comprises at least one step for the transformation of methylmercaptan into dimethyl disulfide by oxidizing methylmercaptan using sulfur.

The present invention also provides a composition based on dimethyl disulfide as defined above, containing, by weight, at least 95% of dimethyl disulfide, less than 500 ppm of methylmercaptan, less than 100 ppm of dimethyl sulfide and 0 to 1% of at least one odor-masking agent selected from vanillin, ethylvanillin and esters.

The present invention also pertains to the use of dimethyl disulfide as defined above for the preparation of methanesulfonic acid. In addition, the present invention pertains to methanesulfonic acid synthesized from dimethyl disulfide as defined above, and in which the bio-carbon content is at least 1%.

The present invention also pertains to a process as defined above further comprising a step for methanesulfonic acid synthesis, in which dimethyl disulfide as defined above is oxidized in the presence of chlorine and hydrolyzed in the presence of water.

The present invention also pertains to a process as defined above further comprising a step for methanesulfonic acid synthesis, in which an alcoholic solution of dimethyl disulfide as defined above is irradiated, in the presence of oxygen, with light at a wavelength in the range 200 to 320 nm.

The present invention also pertains to the use of dimethyl disulfide as defined above as a sulfiding agent, as an anticoking agent, as an intermediate in synthesis, as an anticorrosion agent, as a pesticidal agent, or as a fumigation agent.

DETAILED DESCRIPTION OF EMBODIMENTS OF THE INVENTION

The invention uses products of natural origin as starting substances. The carbon of a biomaterial derives from plant photosynthesis and thus from atmospheric $CO_2$. Degradation (the term "degradation" includes combustion/incineration at the end of life) of such materials to $CO_2$ thus does not contribute to warming since there is no increase in the carbon emitted into the atmosphere. The $CO_2$ balance of biomaterials is thus substantially better and contributes to reducing the carbon footprint of the products obtained (only the energy for manufacture has to be taken into account). In contrast, a material of fossil origin that also degrades to $CO_2$ will contribute to increasing the $CO_2$ level and thus to climatic warming.

The compounds of the invention will thus have a carbon footprint which will be better than that of compounds obtained from a fossil source.

Thus, the invention also improves the ecological balance during the manufacture of DMDS.

The term "bio-carbon" indicates that the carbon is of natural origin and derives from a biomaterial, as indicated below. The bio-carbon content and the biomaterial content are expressions which designate the same value.

A material of renewable origin, also termed a biomaterial, is an organic material in which the carbon derives from recently fixed $CO_2$ (on a human scale) by photosynthesis from the atmosphere. On solid ground, $CO_2$ is captured or fixed by plants. At sea, $CO_2$ is captured or fixed by bacteria or plankton carrying out photosynthesis. A biomaterial (100% carbon or natural origin) has a $^{14}C/^{12}C$ isotope ratio of more than $10^{-12}$, typically of the order of $1.2 \times 10^{-12}$, while a fossil material has a zero ratio. The $^{14}C$ isotope is formed in the atmosphere and is then integrated by photosynthesis over a timescale of at most a few tens of years. The half-life of $^{14}C$ is 5730 years. Thus, materials derived from photosynthesis, namely plants in general, necessarily have a maximum $^{14}C$ isotope level.

The biomaterial content or bio-carbon content is determined by applying ASTM standards D 6866 (ASTM D 6866-06) and D 7026 (ASTM D 7026-04). ASTM standard D 6866 concerns "Determining the Biobased Content of Natural Range Materials Using Radiocarbon and Isotope Ratio Mass Spectrometry Analysis", while ASTM standard D 7026 concerns "Sampling and Reporting of Results for Determination of Biobased Content of Materials via Carbon Isotope Analysis". The first paragraph of the second standard refers to the first one.

The first standard describes a test for measuring the $^{14}C/^{12}C$ ratio of a sample and compares it with the $^{14}C/^{12}C$ ratio of a reference sample of 100% renewable origin, to provide a relative percentage of C of renewable origin in the sample. The standard is based on the same concepts as $^{14}C$ carbon dating, but without applying dating equations.

The ratio calculated thereby is designated as "pMC" (percent Modern Carbon). If the material to be analyzed is a mixture of biomaterial and fossil material (no radioactive isotope), then the value for the pMC obtained is directly correlated to the quantity of biomaterial present in the sample. The reference value used for $^{14}C$ dating is a value dating from the 1950s. This year was selected because of the existence of numerous atmospheric nuclear tests that introduced large quantities of isotopes into the atmosphere after that date. The 1950 reference corresponds to a pMC value of 100. Because of the thermonuclear tests, the actual value to use is approximately 107.5 (which corresponds to a correction factor of 0.93). The radioactive carbon signature of a plant nowadays is thus 107.5. A signature of 54 pMC and 99 pMC thus correspond to a quantity of biomaterial in the sample of 50% and 93% respectively.

ASTM standard D 6866 proposes three techniques for measuring the quantity of $^{14}C$ isotope:

LSC (Liquid Scintillation Counting). This technique consists of counting the "beta" particles derived from disintegration of $^{14}C$. The beta radiation from a sample of known mass (known number of C atoms) is measured over a certain time. This "radioactivity" is proportional to the number of atoms of $^{14}C$, which can then be determined. The $^{14}C$ present in the sample emits radiation that produces photons on contact with a scintillating liquid (scintillator). These photons have different energies (in the range 0 to 156 keV) and form what is referred to as a $^{14}C$ spectrum. In accordance with two variations of this method, the analysis is of either the $CO_2$ previously produced by the carbon-containing sample in an appropriate absorbent fluid, or on benzene after prior conversion of the carbon-containing sample to benzene. ASTM standard D 6866 thus provides two methods, A and C, based on this LSC method;

AMS/IRMS (Accelerated Mass Spectrometry coupled with Isotope Radio Mass Spectrometry). This technique is based on mass spectrometry. The sample is reduced to graphite or gaseous $CO_2$, and analyzed in a mass spectrometer. This technique uses an accelerator and a mass spectrometer to separate $^{14}C$ ions from $^{12}C$ ions and thus to determine the ratio of the two isotopes.

The compounds of the invention at least partially derive from biomaterial and thus have a biomaterial content of at least 1%. This content is advantageously higher, in particular up to 100%. The compounds of the invention may thus comprise 100% bio-carbon or, in contrast, result from a mixture with a compound of fossil origin.

As indicated above, the compounds of the invention are dimethyl disulfides derived at least in part from raw materials of renewable origin.

In order to produce DMDS from bio-carbon, in a first stage a non-sulfided carbon-containing compound is produced: methanol. In a second stage, this non-sulfided compound undergoes sulfiding reactions in order to form a methylmercaptan. In a third stage, the methylmercaptan derived from this methanol is oxidized with sulfur to produce DMDS in accordance with the invention.

Methanol Production

The following reactions may be cited as examples of reactions which are capable of producing non-sulfur-containing compounds based on bio-carbon.

The producing methane from biomass is known. The methane of biogas results from methanization or anerobic digestion of fermentable waste. Regular sources are waste, selective putrescible waste salvage (possibly using digesters), sewage plant sludge, farming effluents, food industry effluents, or from a lake (for example Lake Kivu), etc. Biogas primarily contains methane.

Biomass (fermentation)→$CH_4$

C="renewable carbon"

This methane then undergoes a steam reforming reaction, SMR (Steam Methane Reforming). At the end of this reaction, a mixture of CO and hydrogen in a variable ratio (typically approximately 2) is obtained; it is also termed synthesis gas or syngas.

"renewable carbon"+$H_2O$→CO+$xH_2$ (x is dependent on the C/H ratio of the raw material).

Thus, in the case of methane:

$CH_4$+$H_2O$→CO+$3H_2$

This syngas is used, for example, to produce hydrocarbons by the Fischer-Tropsch process; those hydrocarbons may then be transformed into various products, in particular olefins, using conventional upgrading reactions. Depending on the H$_2$:CO ratio and/or depending on the catalysts used, this syngas may also be transformed into methanol or higher alcohols. Thus, in the case of transformation into methanol:

$$CO + 2H_2 \rightarrow CH_3OH$$

Regarding the transformation of syngas into methanol or a higher alcohol, reference may be made to "Procédés de pétrochimie ["Petrochemical Processes"], IFP, ENSPM", 2$^{nd}$ edition, pp 90-104 and to "Fundamentals of Industrial Catalytic Processes", Wiley, 2$^{nd}$ edition, 6.4.8.

It is also possible to carry out a direct (controlled) oxidation of methane to form methanol directly.

The starting biomass may be a lignocellulosic biomass (wood, sugar cane, straw, etc) or a readily hydrolyzable glucidic biomass (cereals, beet, etc).

Preparation of Methylmercaptan

According to the process of the invention, the methanol obtained thereby is used in preparing methylmercaptan (or methanediol) from hydrogen sulfide and methanol. In said process, hydrogen sulfide and methanol are reacted in the presence of a catalyst.

$$CH_3OH + H_2S \xrightarrow{catalyst} CH_3OH + H_2O$$

This is a known, old reaction, it having been described in 1910 by Sabatier (P Sabatier, A Nailhe, Proceedings 150 823-6, 1569-72, 1217-21, 1910). However, at the time the transformation yields were low, of the order of 50%.

From a quantitative viewpoint, a high degree of methanol transformation and a high selectivity for methylmercaptan should be obtained, i.e. all of the methanol has to react and produce the desired product. In general, at the outlet from the reactor or the series of reactors, a reaction mixture is present that is constituted by non-transformed starting products, mercaptan and by-products such as dimethyl sulfide and dimethyl ether as well as water and inert gases.

According to the conventional method, successive fractional distillations are carried out in order to separate the heavy products from the light products. By this means, it is possible to obtain good degrees of methanol transformation and an acceptable selectivity.

However, a large amount of water then has to be introduced, resulting in effluent which has to be treated, resulting in a loss of energy due to the large amount of distillation.

In order to overcome these problems, then, the method described in patent FR 7 343 539 and FR 2 477 538 is used, which consists of carrying out the synthesis of methylmercaptan by a vapor phase reaction between methanol and hydrogen sulfide at a temperature which is in the range 280° C. to 450° C., preferably in the range 320° C. to 370° C., at all points in the reaction mass, at a pressure in the range 2.5 bar to 25 bar, preferably in the range 7 to 12 bar, the reaction being carried out by passing the reagents over at least three successive beds of catalyst, all of the hydrogen sulfide being introduced to the first bed and a fraction of the total methanol being introduced to each bed, and with the overall molar ratio of hydrogen sulfide to total methanol being in the range 1.10 to 2.5.

Separation of the products containing sulfur and the products not containing sulfur is carried out on the mixture from the reaction.

In practice, a pre-condensation and decantation reaction is advantageously carried out at the outlet from the last reactor in order to obtain an organic phase principally constituted by the sulfur-containing products and an aqueous phase constituted by products not containing sulfur which are separated from each other.

The organic phase is then distilled under pressure in order to eliminate hydrogen sulfide overhead, then the bottoms mixture is depressurized and a fresh distillation is carried out on it, the mercaptan being recovered overhead from this second distillation.

In accordance with a particular form of the invention, the bottoms product which contains dimethyl sulfide may advantageously be recycled to the reaction after extraction of residual unreacted alcohol.

Similarly, the hydrogen sulfide recovered overhead from the first distillation may be sent to the reaction head.

In accordance with one implementation of the invention, the aqueous phase resulting from the pre-condensation and decantation step undergoes a distillation with an optional recycle of the alcohol recovered thereby to the reaction.

Similarly, the vapors derived from the reaction mixture may be washed with methanol in order to liberate the mercaptan from its hydrates.

There is no fixed upper limit to the number of catalytic beds, but technical and economic constraints mean that the number should be no higher than about 15.

Although all of the hydrogen sulfide is introduced to the first bed of catalyst, the methanol is injected in fractions to the inlet to each catalyst zone. The fractions may be distributed evenly or unevenly over the set of beds. It is also possible to distribute all of the methanol feed over the set of beds less a few units in order to use these latter as reaction finishers. As an example, the catalytic mass may be divided into ten successive beds, the methanol feed being divided into nine equal portions each introduced to the first nine beds, the last bed being used to complete the reaction.

In accordance with a preferred implementation, the methanol introduction device is selected so as to be capable of injecting partially in the liquid form and partially in the gaseous form.

The heat of evaporation of methanol thus means that all or part of the heat released by the reaction can be absorbed. By bringing the proportion of methanol introduced in the liquid form under the control of the inlet temperature of the reagents into the catalytic bed concerned, it is also possible to control the reaction temperature most effectively.

A further characteristic consists of selecting an overall H$_2$S/CH$_3$OH molar ratio in the range 1.10 to 2.5. By means of the multi-injection technique described above, it is possible to obtain a high selectivity for methylmercaptan despite the low molar ratio selected. This characteristic is important from the economic viewpoint as it means that the number of reactors, lines, pumps, etc can be reduced.

Another characteristic consists of selecting an activated alumina with a specific surface area in the range 100 to 350 m$^2$/g as a catalyst.

Further, in order to further improve the selectivity of the reaction, it is possible to use a promoter. Any of the promoters proposed in the literature may be suitable for carrying out the invention. However, it is of advantage to select the most effective, in particular metallic sulfides such as cadmium sulfide or potassium salts and oxides such as the carbonate or the tungstate.

The fraction containing the dimethyl sulfide may be recycled in whole or in part to the reaction step.

If it is recycled, it is advantageous to use for this purpose the first reactor into which all of the hydrogen sulfide is introduced. However, in a variation of the implementation, it is possible to use an independent transformation reactor.

The catalyst used for this reaction is preferably an activated alumina with a specific surface area in the range 100 to 400 m²/g in the form of 2 to 5 mm diameter beads. The temperature is in the range 280° C. to 450° C., preferably in the range 350° C. to 450° C., and at a pressure in the range 2.5 to 25 bars.

In the context of carrying out the process of the invention, the pressure at the first distillation step is in the range 5 to 30 bars, preferably in the range 10 to 20 bars, while in the second distillation step, it is 1 to 5 bars, preferably in the range 1.5 to 3 bars.

In accordance with an alternative implementation, the methylmercaptan synthesis may also be carried out directly from synthesis gas (syngas) produced in accordance with the reactions described above, starting from biomass. In this case, the methylmercaptan synthesis is carried out by direct reaction of synthesis gas with hydrogen sulfide in accordance with a catalytic process, and without passing via methanol. The overall reaction in this case can be written as follows:

$$CO + 2H_2 + H_2S \rightarrow CH_3SH + H_2O$$

According to the process of the invention, the mercaptan obtained thereby is used in the manufacture of dimethyl disulfide.

Manufacture of Dimethyl Disulfide

One important access route to organic disulfides consists of oxidizing mercaptans using sulfur in the presence of a catalyst.

When a mercaptan (RSH) and sulfur are brought into the presence of a catalyst, the corresponding disulfide is obtained in accordance with the following reaction scheme:

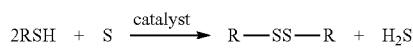

employing one atom of sulfur, S, for every two molecules of mercaptan.

Formation of the disulfide R—SS—R is generally accompanied by the formation of secondary products, namely polysulfides with a structure analogous to the disulfide but containing a larger number of combined sulfur atoms (R—Sn—R where n>2).

The reactions resulting in polysulfides may represented by the following equations:

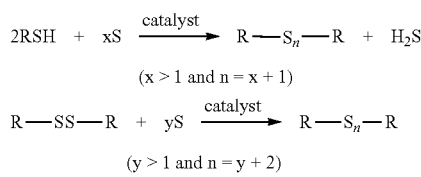

It is known that polysulfides (R—Sn—R) may be converted to disulfides (R—SS—R) by reaction with the mercaptan, RSH. These reactions may be represented as follows:

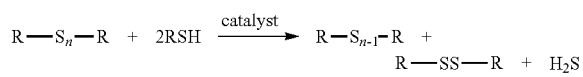

-continued

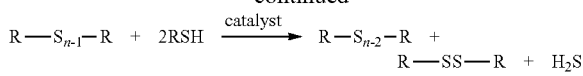

etc. . . . .

In the case in which the polysulfides are completely converted to disulfides, the general equation for this conversion may be set out as follows:

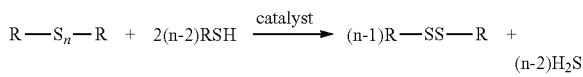

This reaction for conversion of a polysulfide into a disulfide was exploited in U.S. Pat. No. 3,299,146 for a process for preparing dimethyl disulfide that consisted of reacting methylmercaptan with dimethyl trisulfide:

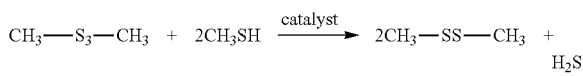

Processes for the continuous manufacture of dialkyl disulfides from alkylmercaptans and sulfur, which are described in patents EP 0 202 420 and EP 0 337 839, use a synthesis reactor into which the mercaptan and sulfur are introduced. The polysulfides formed in the reaction for oxidation of the mercaptan by sulfur are recycled to the synthesis reactor for conversion into disulfide, after having separated the disulfide by distillation. This continuous recycling has the result of increasing the polysulfide content in the reactor and reducing the disulfide yield, and finally of requiring a distillation column with dimensions and features that are adapted to the compositions of the polysulfide-rich reaction products. In the case of the manufacture of dimethyl disulfide from methylmercaptan and sulfur, the examples described in the European patents cited above effectively show that the synthesis reactor produces fairly large quantities of dimethyl polysulfides.

According to the present invention, which concerns a process for the manufacture of dimethyl disulfide, it is much more advantageous to carry out the conversion (or retrogradation) reaction of dimethyl polysulfides to dimethyl disulfide in an independent reactor, as described in EP 0 446 109, the yields under these conditions being much higher than in the case of a recycle to the synthesis reactor. Furthermore, the presence of hydrogen sulfide in the reagents introduced into the retrogradation reactor has an unfavorable effect on the dimethyl polysulfides to dimethyl disulfide transformation yield and prior elimination of hydrogen sulfide means that almost complete conversion to dimethyl disulfide is achieved.

Advantageously, the process of the invention for the manufacture of dimethyl disulfide from methylmercaptan of at least partially renewable origin and sulfur comprises two reaction zones and an intermediate degassing zone. The first reaction zone is supplied with reagents (methylmercaptan and sulfur) which, in the presence of a catalyst (optionally introduced simultaneously with the reagents), react together to produce dimethyl disulfide and dimethyl polysulfides.

The degassing zone is located downstream of the first reaction zone and acts to eliminate the hydrogen sulfide contained in the unrefined liquid products leaving the first reaction zone. Although it is preferable to eliminate the hydrogen sulfide as completely as possible, the scope of the present invention encompasses eliminating only a portion (at least 50%) of the hydrogen sulfide. This degassing operation may be carried out either by heating the products or by entrainment using an inert gas, optionally combined with heating, at a pressure which is higher than atmospheric pressure up to 10 bar, preferably below 6 bar.

The second reaction zone, supplied with products deriving from the degassing zone after eliminating at least 50% of the hydrogen sulfide, is aimed at converting the dimethyl polysulfides into dimethyl disulfide by reaction with methylmercaptan in the presence of a catalyst.

In accordance with one implementation for the manufacture of dimethyl disulfide from methylmercaptan, a layout schematic is used that comprises a first reactor 1 (primary reactor), a degasser 2, a complementary second reactor 3 (finishing reactor), a degassing column 4 for complete elimination of the hydrogen sulfide from the reaction products before rectification thereof, and a distillation section 5 and 6.

The reagents: sulfur (liquid or solid) and methylmercaptan (liquid) in excess with respect to the stoichiometry, are introduced into the reactor 1 via two respective lines. In the case in which the reaction catalyst is simultaneously incorporated, it is introduced via a single line. The gaseous effluents which may be formed in the reactor are optionally eliminated via another line, and the unrefined liquid reaction product, withdrawn from reactor 1, is supplied to the degasser 2 via a line. The residence time in the reactor 1 is adjusted in known manner in order to obtain at its outlet almost complete conversion of the sulfur initially introduced, i.e. a conversion equal to 100% or at least such that the non-transformed sulfur is dissolved in the liquid effluent.

The degasser 2 is equipped for selective elimination of the hydrogen sulfide dissolved in the liquid which derives from reactor 1, either by heating or by entrainment in an inert gas introduced via a line.

The liquid, freed of hydrogen sulfide, is withdrawn from the bottom of the degasser and is supplied via a line to the finishing reactor 3 in which the dimethyl polysulfides formed in the reactor 1 are converted into dimethyl disulfide in the presence of the catalyst by reaction with excess methylmercaptan. The residence time in the reactor 3 is adjusted in a manner that is known per se, as a function of the amount of dimethyl polysulfides which can be accepted in the effluent; a longer residence time favors retrogradation of dimethyl polysulfides to dimethyl disulfide.

The products leaving the reactor 3 are supplied to the degassing column 4 for complete elimination of dissolved hydrogen sulfide either by heating or by entrainment in an inert gas introduced via a line.

The distillation section is supplied with products leaving the degassing column 4 for separation in the column 5 of methylmercaptan contained in the product with a view to recycling it to the reactor 1. The product recovered from the bottom of the column 5 is supplied via a line to the head of the column 6 from which dimethyl disulfide is recovered, while the column bottoms from 6, constituted by non-transformed dimethyl polysulfides mixed with dimethyl disulfide, are preferably recycled to the finishing reactor 3. One possible variation consist of returning the bottoms from column 6 to the reactor 1.

The device described above corresponds to the simplest embodiment. The skilled person will understand that the scope of the present invention encompasses using a first reaction zone constituted by several reactors functioning in parallel and connected to the same degasser or to a plurality of degassers constituting an intermediate degassing zone.

Similarly, the scope of the present invention encompasses using a second reaction zone constituted by several finishing reactors. Thus, for example, in order to improve the dimethyl disulfide yield and avoid recycling dimethyl polysulfides, several finishing reactors disposed in series may be used, each preceded by an intermediate degasser allowing the hydrogen sulfide formed in the preceding reactor to be eliminated.

This step of the process of the invention may be carried out with different types of reactors, for example stirred and/or tube reactors; the choice between these may depend on the reaction conditions and the nature of the catalysts employed.

As is the case in known processes, the methylmercaptan/sulfur molar ratio must be at least 2. Since a large excess of methylmercaptan favors the selectivity for dimethyl disulfide, the methylmercaptan/sulfur ratio may be in the range 2 to 10; preferably, it is in the range 3 to 6 in order to minimize the quantities of methylmercaptan to be separated and recycled.

Each of the reaction zones is operated at pressures above atmospheric pressure. The pressure must be at least sufficient to maintain the methylmercaptan in the liquid state and may be up to 50 bars.

The process of the invention may be carried out in a wide temperature range depending on the nature of the catalysts employed. The temperature may be in the range 25° C. to 150° C. in the case of thermally stable catalysts.

Any of the catalysts known in the prior art for the oxidation of mercaptans by sulfur may be used in the process of the invention, whether they be liquid or solid, organic or inorganic basic agents such as alkaline bases, alkaline alcoholates, alkaline mercaptides, combinations of alkaline bases with a mercaptan and an alkene oxide, amines in the free state or bound to organic supports (organic anion exchange resins), or whether they be mineral oxides of certain metals such as magnesium oxide or aluminosilicates such as zeolites. The catalysts may be identical in the two reaction zones, or they may be different.

Given the technical and economic advantages of using sulfur in the liquid state when introducing it into the synthesis reactors, the choice of catalyst may determine the type of primary reactor (reactor 1) to be used in the process of the invention.

In the case in which catalysts with a limited thermal stability are used, such as anion exchange resins with tertiary amine functions, examples of which being Amberlyst A21, IRA 93 SP and IRA 94 S, which cannot be used at temperatures exceeding 100° C., introducing liquid sulfur (melting point of sulfur from approximately 113° C.) means that a stirred reactor must be used as the primary reactor (reactor 1), in which the catalyst is in suspension in the liquid medium. The reaction between the methylmercaptan and the sulfur must be carried out at a temperature below 100° C. in the presence of these resins as catalysts.

In the case in which solid catalysts are used that have a low attrition resistance, the use of a stirred reactor as the primary reactor (reactor 1) should be avoided. If these catalysts are thermally stable, their use in a fixed bed tube reactor as the primary reactor (reactor 1) is the most appropriate technical solution; in this case the reaction temperature must be higher than the melting point of sulfur.

In the case in which homogeneous, stable liquid catalysts are employed, the primary reactor (reactor 1) may be either of the stirred type or of the tube type. This type of catalyst is introduced into the primary reactor simultaneously with the methylmercaptan and sulfur reagents and in this case it acts as a catalyst for the finishing reactor (reactor 3) in the process of the invention, which may be either of the stirred type or of the tube type.

In contrast, in the case in which the primary reactor (reactor 1) contains a charge of solid catalyst which is insoluble in the reaction medium, the solid catalyst used in the finishing reactor (reactor 3) may be identical or different. Depending on the nature of the catalyst used, the finishing reactor 3 may be of the stirred or tube type; in the case of a solid catalyst with a low attrition resistance, the reactor will preferably be a fixed bed tube reactor.

This oxidation of methylmercaptan by sulfur, catalyzed by homogeneous or heterogeneous, organic or inorganic basic agents, continuously or batchwise, is accompanied by a release of hydrogen sulfide as well as dimethyl polysulfides ($CH_3S_xCH_3$) with a sulfur chain of more than 2. In order to manufacture DMDS in high yields and with a limited production of DMPS (dimethyl polysulfides with a sulfur chain of more than 2), the preparation process described above, comprising two reaction zones interrupted by an intermediate degassing zone and followed by a distillation zone, is particularly suitable. However, although it performs well in terms of yield and DMDS selectivity, this process may leave in the finished product a non-negligible quantity of methylmercaptan (approximately 4000 ppm) as well as a very small quantity of dimethyl sulfide (approximately 300 ppm) deriving from the methylmercaptan used or produced during synthesis of the DMDS. The result of these volatile impurities is that they result in a very disagreeable and aggressive odor for the DMDS and this strong odor is considered to be a major inconvenience to consumers when handling this product.

Adding an odor-masking agent is only effective if the DMDS used has reduced quantities of volatile strong-smelling impurities such as methylmercaptan and dimethyl sulfide and preferably contains less than 200 ppm by weight of methylmercaptan and less than 50 ppm by weight of dimethyl sulfide. The most effective odor-masking agents are described in patent EP 0 976726. These odor-masking agents are selected from esters with the general formula (I): $R^1CO_2R^2$, in which $R^1$ represents a linear or branched hydrocarbon radical containing 1 to 4 carbon atoms that may be unsaturated, and $R^2$ represents a linear, branched or cyclic hydrocarbon radical containing 2 to 8 carbon atoms that may be unsaturated.

The invention also pertains to a composition based on DMDS manufactured at least in part from raw materials of renewable origin, characterized in that it contains, by weight, at least 95% of dimethyl disulfide, less than 500 ppm of methylmercaptan (MM), less than 100 ppm of dimethyl sulfide (DMS) and 0 to 1% of at least one odor-masking agent selected from vanillin, ethylvanillin and preferably esters with general formula (I).

Advantageously, any method which is known to the skilled person for obtaining DMDS with reduced quantities of volatile impurities such as MM and DMS may be used in the context of the present invention. However, in the case of a DMDS containing high levels of MM and DMS, a particularly preferred method consists of topping by distillation. This method has the advantage of eliminating MM and DMS jointly, while normal methods for odor reduction, generally based on the elimination of residual mercaptans by specific reaction of the mercaptan function with an elimination agent such as a base or an alkene oxide in the presence of a base, have no effect on the DMS present in the DMDS.

The topped DMDS, preferably containing less than 200 ppm of MM and less than 50 ppm of DMS, is used to prepare a composition of the invention.

Advantageously, the composition of the invention comprises at least one odor-masking agent.

Since one of the principal advantages of DMDS in its applications is its high sulfur content (68%), too much odor-masking agent in the composition would lead to a reduction in this sulfur titer and would reduce the advantage of this product for its principal applications. The maximum quantity of odor-masking agent(s) is thus fixed at 1%, but this quantity is preferably in the range 0.1% to 0.5% and more particularly equal to 0.2%.

Illustrative but non-limiting examples of esters with general formula (I) which may be cited are butyl, isoamyl or benzyl acetates and ethyl, propyl, butyl, 2-methylbutyl or isoamyl butyrates. Isoamyl acetate, 2-methylbutyl butyrate, isoamyl butyrate, benzyl acetate and mixtures of these compounds are particularly preferred. The esters (I) may or may not be associated with orthophthalates, such as diethyl orthophthalate.

A non-limiting example of a composition according to the present invention comprises, by weight:

| | |
|---|---|
| isoamyl acetate | 0.1% |
| diethyl orthophthalate | 0.1% |
| topped DMDS | 99.8%. |

Another composition according to the present invention comprises, by weight:

| | |
|---|---|
| isoamyl acetate | 0.05% |
| 2-methylbutyl butyrate | 0.03% |
| benzyl acetate | 0.02% |
| diethyl orthophthalate | 0.1% |
| topped DMDS | 99.8%. |

Manufacture of Methanesulfonic Acid

The present invention also pertains to the use of DMDS obtained using the process of the invention for the synthesis of methanesulfonic acid.

Alkanesulfonic acids such as methanesulfonic acid and their salts have numerous industrial applications, in particular as detergents, emulsifiers, esterification catalysts, or hardeners for certain resins.

The dimethyl disulfide of the invention in accordance with that defined above is oxidized in the presence of chorine and hydrolyzed in the presence of water under conditions known to the skilled person, and as described in U.S. Pat. No. 5,583,253. The methylmercaptan reacts with chlorine in the presence of aqueous hydrochloric acid at a high temperature of about 85° C. to 115° C., preferably about 95° C. to 105° C., and in general about 98° C. At the end of this process, the aqueous methanesulfonic acid (hereinafter abbreviated to MSA) may contain non-negligible quantities of stable intermediates such as DMDS, methane methylthiosulfonate (hereinafter abbreviated to MMTS) and methanesulfonyl chloride (hereinafter abbreviated to MSC). The total quantity of DMDS and MMTS is given the term "oxidizable impurities" in the product characteristics. These impurities may be reacted with hydrogen peroxide or ozone by post-treatment of the aqueous MSA product using these agents.

The unrefined aqueous MSA containing the oxidizable impurities may be treated with chlorine in sufficient quantity to convert said oxidizable impurities to MSC, and the MSC containing aqueous MSA is subjected to sufficient heat to hydrolyze the MSC to MSA. As described in U.S. Pat. No. 5,583,253, the quantity of chlorine used is adapted to whether the unrefined MSA is treated with chlorine as part of a continuous or batch process.

The unrefined aqueous MSA is generally passed through a stream of vapour or the like to remove the residual impurities from the unrefined aqueous MSA. Once the chlorides, DMDS, MMTS, MSC, water and uncondensed chlorine have been removed thereby, an aqueous MSA is recovered as the product wherein the oxidizable impurities have been substantially reduced. MSC, which is produced by converting oxidizable impurities with chlorine, is hydrolyzed to MSA in the vapor stream.

In an alternative to the hydrolysis of MSC in a vapor stream, a finishing reactor subjects the MSC which is in the unrefined aqueous MSA to sufficient heat for a sufficient time to convert the MSC to MSA. The product from the finishing reactor may also be subjected to a stream of vapor if required.

Although chlorination of the unrefined aqueous MSA is preferably carried out in the reactor discharge line or pipework, as close as possible to the reactor, advantageous purification results may be obtained by injecting chlorine into the effluent at any point of the process after the reactor outlet, provided that the chlorine is in appropriate contact with the oxidizable impurities to react and form MSC so that the MSC can be hydrolyzed to MSA. Different alternative points for injecting chlorine into the aqueous MSA may thus be employed. If necessary, the purified aqueous MSA is treated further to remove practically all of the water, for example using the evaporation procedures described in U.S. Pat. No. 4,450,047 or U.S. Pat. No. 4,938,846.

Industrially, the alkanesulfonic acids thus usually manufactured from alkanes by sulfooxidation or sulfochlorination. These two synthesis pathways may occasionally lead to the formation of by-products sulfonated on the various carbon atoms of the hydrocarbon chain. Further, hydrolysis of alkanesulfochlorides may produce alkanesulfonic acids which are colored to a greater or lesser extent, necessitating a final decolorization treatment, for example using chlorine.

Excellent alkanesulfonic acid yields may be obtained by photooxidation of dialkyl disulfides in the presence of oxygen without a catalyst if the operation is carried out in solution in an alcohol with a light source irradiating between 200 and 320 nm. This photooxidation which is described in patent EP 0 627 414, employs the following reaction:

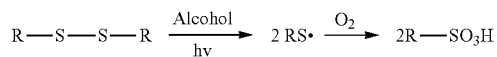

$$R-S-S-R \xrightarrow[h\nu]{\text{Alcohol}} 2\,RS\cdot \xrightarrow{O_2} 2R-SO_3H$$

There is also an advantage in producing acids the sulfonic acid group of which is exclusively fixed to the end of the hydrocarbon chain.

In accordance with this implementation of the process for preparing a methanesulfonic acid, R—SO$_3$H, from dimethyl disulfide, DMDS, of the invention, an alcoholic solution of dimethyl disulfide containing no methylene blue as a photosensitizer is subjected, in the presence of oxygen, to irradiation with light at a wavelength in the range 200 to 320 nm.

The alcohol used may advantageously be selected from primary, secondary or tertiary alcohols containing 1 to 12 carbon atoms. However, a C1 to C4 alcohol, and more particularly methanol, is preferably used. The methanol used is advantageously that synthesized from renewable materials, as described above. The DMDS content of the alcoholic starting solution may vary within a wide range depending on the alcohol employed. It is generally from 0.1% to 90% by weight, but is preferably in the range 2% to 25%.

The oxygen necessary for the reaction may be supplied in the pure form or diluted by an inert gas such as nitrogen, for example. The oxygen is preferably progressively introduced into the alcoholic solution. The total quantity of oxygen required is at least 4 moles per mole of DMDS present in the initial solution, but it is preferable to operate with an excess of oxygen of at least 50%.

Photooxidation may be carried out at a temperature in the range –20° C. to the boiling point of the alcohol, but preferably in the range 18° C. to 45° C. The operation is advantageously carried out at atmospheric pressure, but the scope of the invention encompasses operating under slight pressure.

This implementation of the process of the invention may be carried out continuously or batchwise, in any photochemical reactor, for example in an immersion reactor or in a falling film reactor, provided with one or more mercury vapor lamps at low, medium or high pressure, or excimer lamps emitting in the ultraviolet.

The invention claimed is:

1. A process for the preparation of dimethyl disulfide (DMDS) from a biomass which comprises
   (1) fermenting the biomass to produce methane;
   (2) steam reforming said methane to form a synthesis gas;
   (3) producing methylmercaptan directly from said synthesis gas by reacting said synthesis gas with hydrogen sulfide;
   (4) oxidizing the methylmercaptan obtained at step (3) to produce DMDS; and
   (5) obtaining DMDS having a bio-carbon content of at least 1%.

2. A process for the preparation of methanesulfonic acid from biomass which comprises the following steps:
   (1) fermenting the biomass to produce methane;
   (2) steam reforming to form a synthesis gas;
   (3) producing methylmercaptan directly from said synthesis gas by reacting said synthesis gas with hydrogen sulphide;
   (4) oxidizing methylmercaptan obtained at step (3) to produce DMDS;
   (5) oxidizing the dimethyl disulfide obtained at step (4) in the presence of chlorine and hydrolyzing in the presence of water to produce the methanesulfonic acid; and
   (6) obtaining methanesulfonic acid having a biocarbon content of at least 1%.

3. The process as claimed in claim 2, further comprising a step for methanesulfonic acid synthesis, in which an alcoholic solution of the dimethyl disulfide is irradiated, in the presence of oxygen, with a wavelength in the range 200 to 320 nm.

4. The process as claimed in claim 1, wherein step (4) is performed in the presence of chlorine.

* * * * *